US012780684B2

(12) United States Patent
Schleiffarth et al.

(10) Patent No.: US 12,780,684 B2
(45) **Date of Patent: *Nov. 3, 2026**

(54) SYSTEMS AND METHODS FOR TREATING BIOLOGICALLY CONTAMINATED WATER STREAMS

(71) Applicant: VACOM SYSTEMS, LLC, Park City, UT (US)

(72) Inventors: James W. Schleiffarth, Midway, UT (US); Lance Edling, Park City, UT (US); Larry Sanderson, Park City, UT (US)

(73) Assignee: Vacom Systems, LLC, Park City, UT (US)

( * ) Notice: Subject to any disclaimer, the term of this patent is extended or adjusted under 35 U.S.C. 154(b) by 68 days.

This patent is subject to a terminal disclaimer.

(21) Appl. No.: 18/667,758

(22) Filed: May 17, 2024

(65) Prior Publication Data

US 2025/0042773 A1 Feb. 6, 2025

Related U.S. Application Data

(63) Continuation of application No. 17/665,491, filed on Feb. 4, 2022, now Pat. No. 12,012,339.

(Continued)

(51) Int. Cl.

*C02F 1/06* (2023.01)
*B01D 1/14* (2006.01)

(Continued)

(52) U.S. Cl.

CPC .................. *C02F 1/06* (2013.01); *B01D 1/14* (2013.01); *B01D 1/28* (2013.01); *B01D 1/284* (2013.01);

(Continued)

(58) Field of Classification Search

CPC .... C02F 1/02–18; C02F 2303/04; C12N 1/06; C12N 1/063; C12N 1/066

See application file for complete search history.

(56) References Cited

U.S. PATENT DOCUMENTS 1,461,640 A 7/1923 Wirth-Frey
5,785,852 A 7/1998 Rivard (Continued)

FOREIGN PATENT DOCUMENTS

JP H049801 A 1/1992
JP 2000107747 A 4/2000

(Continued)

OTHER PUBLICATIONS

Foladori, Paola; "Sludge Reduction Technologies in Wastewater Treatment Plants;" International Water Association Publishing [online]; Jul. 31, 2010; [retrieved on May 6, 2022]; pp. 32, 178, 210, 50, 18, 29-32, 226, 218. DOI: 10.2166/9781780401706.

(Continued)

*Primary Examiner* — Jonathan Luke Pilcher

(57) ABSTRACT

A system for treating a biologically contaminated water stream to lyse pathogens within the biologically contaminated water stream is provided. The system can include a flash vessel configured to receive a biologically contaminated water stream and to separate steam from liquid in the biologically contaminated water stream, a blower configured to receive the separated steam from the flash vessel and compress the separated steam for reintroduction into the biologically contaminated water stream, a circulation pump configured to receive the separated liquid from the flash vessel and to pressurize the separated liquid into a circulation stream, a preheater exchanger configured to receive treated water from the circulation stream and preheat the biologically contaminated water stream, and a pressure drop (Continued)

device configured to lower the pressure of the biologically contaminated water stream prior to receipt by the flash vessel.

5 Claims, 3 Drawing Sheets

Related U.S. Application Data

(60) Provisional application No. 63/145,912, filed on Feb. 4, 2021.

(51) Int. Cl.

| | |
|---|---|
| ***B01D 1/28*** | (2006.01) |
| ***B01D 1/30*** | (2006.01) |
| ***B01D 3/00*** | (2006.01) |
| ***B01D 3/06*** | (2006.01) |
| ***C02F 11/18*** | (2006.01) |
| ***C12N 1/06*** | (2006.01) |
| ***C12N 1/066*** | (2026.01) |

(52) U.S. Cl.

CPC ............. *B01D 1/305* (2013.01); *B01D 3/007* (2013.01); *B01D 3/06* (2013.01); *C02F 11/18* (2013.01); *C12N 1/06* (2013.01); *C12N 1/066* (2013.01); *C02F 2301/046* (2013.01); *C02F 2303/04* (2013.01); *C02F 2303/10* (2013.01)

(56) References Cited

U.S. PATENT DOCUMENTS

| | | | | |
|---|---|---|---|---|
| 5,968,321 | A | 10/1999 | Sears | |
| 6,365,005 | B1 | 4/2002 | Schleiffarth | |
| 6,977,047 | B2 | 12/2005 | Nunez | |
| 10,434,435 | B2 | 10/2019 | Mack | |
| 11,649,174 | B2 | 5/2023 | Schleiffarth | |
| 12,012,339 | B2 * | 6/2024 | Schleiffarth | C02F 11/18 |
| 2003/0132095 | A1 * | 7/2003 | Kenet | C02F 1/04 203/1 |
| 2005/0056594 | A1 | 3/2005 | Nunez | |
| 2010/0239712 | A1 | 9/2010 | Brooks | |
| 2012/0061318 | A1 | 3/2012 | Buchmuller | |
| 2014/0283717 | A1 | 9/2014 | Bolin | |
| 2015/0360971 | A1 | 12/2015 | Schleiffarth | |
| 2019/0099689 | A1 | 4/2019 | Mack | |

FOREIGN PATENT DOCUMENTS

| | | | |
|---|---|---|---|
| JP | 2005-161140 | A | 6/2005 |
| JP | 2017-525557 | A | 9/2017 |
| KR | 200227278 | Y1 | 6/2001 |

OTHER PUBLICATIONS

Matsuura, Yusuke, "Notice of Reasons for Refusal", Japanese Patent Application No. 2023-547612, mailed Dec. 2, 2025, 10 pages.

Yoon, Jaek W., "Search Report", United Arab Emirates Patent Application No. P6001971/2023, mailed Feb. 12, 2026, 9 pages.

Unknown, "First Examination Report", Saudi Arabian Patent Application No. 523450184, mailed Sep. 10, 2025, 18 pages.

Unknown, "Second Examination Report", Saudi Arabian Patent Application No. 523450184, mailed Dec. 11, 2025, 14 pages.

* cited by examiner

SYSTEMS AND METHODS FOR TREATING BIOLOGICALLY CONTAMINATED WATER STREAMS

PRIORITY CLAIM

This application is a continuation of U.S. patent application Ser. No. 17/665,491, filed Feb. 4, 2022, which claims priority to United States Provisional Patent Application No. 63/145,912, filed on Feb. 4, 2021, each of which is incorporated herein by reference in its entirety.

BACKGROUND

The present disclosure is directed to treatment of biologically contaminated water such as biologically contaminated water in municipal or industrial water treatment facilities. More specifically, the present disclosure is directed to systems and methods for cell lysis of biologically contaminated water, the destruction of pathogens in the biologically contaminated water, and dewatering a biologically contaminated water stream.

Contaminated water having high levels of organic material measured in terms of Biological Oxygen Demand (BOD) often use a biological treatment process to remove organic material from the contaminated water. This process creates an environment favorable for exponential growth of biological organisms (primarily bacteria) that utilize the organic waste in the contaminated water for cell reproduction. The result of a biological treatment process is that the organic material is removed from the water (BOD levels in the water decrease) and a large population of biological organisms are created. One type of biomass that is created is often referred to as activated sludge. The excess biomass that is produced is referred to as waste activated sludge (WAS).

One problem associated with such a biological treatment process concerns the final disposal of the solids in the contaminated waste. WAS, or the biomass that is no longer needed within the biological treatment process is generally disposed either as a reusable product (as a fertilizer) or at a landfill. However, WAS is not a simple waste product to dispose. This is because WAS contains pathogens (disease causing bacteria), and it readily retains water. Therefore, it is difficult to reduce the overall volume of the WAS using traditional water separation technologies. The disposal of WAS is an abundant problem as nearly every municipal wastewater treatment plant in the United States creates WAS daily (approximately 16,000 locations).

In many locations around the USA, WAS is dewatered to approximately 20% solid content and 80% water content. Then it is shipped to a landfill for disposal. Larger municipal plants will often employ digesters to process the WAS which creates some natural gas for energy production, slightly reduces final disposal volumes, and most importantly, destroys the pathogens rendering the WAS safer for reuse applications. However, even when digesters are employed, dewatering the WAS does not improve. That is, there still remains about a 20% solids to 80% water ratio.

If a standard sized wastewater treatment plant (just 1 of the 16,000 systems in the USA) produces 3,000 lbs/day of dry WAS, this means that approximately 15,000 lbs/day of the dewatered WAS will be shipped off for reuse or disposal. Disposal costs for WAS at landfill sites around the US is rising and is regularly above $50/ton. This presents a significant cost for wastewater treatment plants around the country.

SUMMARY

The present inventors have recognized that it would be advantageous to develop a system that can condition sludge like a digester by destroying pathogens. Additionally, a system is also needed that can allow WAS to be dewatered to a higher solids/water ratio, thereby reducing disposal costs and increasing reuse possibilities.

The systems and methods set forth in the present disclosure are operable to treat and condition a biological wastewater stream (such as WAS) with up to or greater than about a 4% solids to 96% water ratio. With the biological wastewater stream so conditioned, it is ready for further treatment either through a digester and/or dewatering technology. The systems and methods set forth herein enhance both a digestion and a dewatering process. For an application using a digester, the systems and methods can improve the processing rate thereby allowing the digester to process larger flows within a smaller sized digester. As another advantage, when used in conjunction with an anaerobic digester, an additional 25% increase in the generation of bio-gas (methane) is expected. Furthermore, when used in conjunction with either an aerobic or anaerobic digester, an additional 25% reduction in the generation of solids is expected. For dewatering, the systems and methods can improve the dewaterability of the biological wastewater stream to reduce the overall volume of the material to be disposed. It is estimated that the benefits of improved digestion and dewatering outweigh the additional operating and energy costs associated with the systems and methods set forth herein.

In one example, a system for treating a biological wastewater stream to lyse pathogens within the biological wastewater stream is provided. The system can include a flash vessel configured to receive a biological wastewater stream and to separate steam from liquid in the biological wastewater stream, a blower configured to receive the separated steam from the flash vessel and compress the separated steam for reintroduction into the biological wastewater stream, a circulation pump configured to receive the separated liquid from the flash vessel and to pressurize the separated liquid into a circulation stream, a preheater exchanger configured to receive treated water from the circulation stream and preheat the biological wastewater stream, and a pressure drop device configured to lower the pressure of the biological wastewater stream prior to receipt by the flash vessel.

In one example, the system can further comprise a mist separator disposed between the flash vessel and the blower. The mist separator can be operable to extract liquid from the separated steam.

In one example, the biologically contaminated water stream is joined with the circulation stream between the circulation pump and the pressure drop device. The treated water can be separated from the circulation stream between the pump and the joining of the circulation stream and the biologically contaminated water stream. A heat exchanger can further be provided that is operable to further heat the biologically contaminated water stream prior to being directed to the pressure drop device.

In another example, a system for treating a biologically contaminated water stream to lyse pathogens within the biologically contaminated water stream is provided. The system can comprise a heat source configured to add heat to a circulation stream comprising a biologically contaminated water stream comprising pathogens and solids, a flash vessel configured to receive the circulation stream and to separate steam from liquid from the circulation stream, and a blower configured to receive the separated steam from the flash vessel. The blower can compress the separated steam which can then be reintroduced into the circulation stream to recover latent heat of evaporation.

The system can further comprise a circulation pump configured to receive the separated liquid from the flash vessel and to pressurize the separated liquid into the circulation stream and a pressure drop device configured to lower the pressure of the circulation stream prior to the circulation stream being received by the flash vessel. The pressure drop device and the circulation pump can cause break down of cell walls of the pathogens within the circulation stream. The system can further comprise a preheater exchanger configured to receive treated water from the circulation stream to preheat input water to be added to the circulation stream to recover heat from the treated water.

In one example, the heat source is a heat exchanger. In another example, the heat source comprises the addition of makeup steam to the circulation stream.

In one example, the separated steam is reintroduced into the circulation stream between the flash vessel and the circulation pump.

In another example, a method of harvesting water from a pathogen in a biologically contaminated water steam is provided. The method comprises preheating a biologically contaminated water stream using heat from a treated water stream, adding the preheated biologically contaminated water stream to a circulation stream, pressurizing and adding heat to the circulation stream, dropping the pressure of the circulation stream, separating steam from liquid in the circulation stream, compressing the steam and reintroducing the steam into the circulation stream, and outputting the treated water stream from the circulation stream.

In one example, the circulation stream is pressurized between the separating of the steam from the liquid and the adding of the preheated biologically contaminated water stream to the circulation stream.

In one example, the method can further comprise adding additional heat to the circulation stream after adding the preheated biologically contaminated water stream to the circulation stream. The method can also comprise extracting a liquid stream from the steam prior to compressing the steam and adding the liquid stream to the circulation stream. In one example, the steam can be reintroduced to the circulation stream prior to pressuring the circulation stream.

BRIEF DESCRIPTION OF THE DRAWINGS

Additional features and advantages of invention embodiments will be apparent from the detailed description which follows, taken in conjunction with the accompanying drawings, which together illustrate, by way of example, features of the invention; and, wherein.

Figure 1:
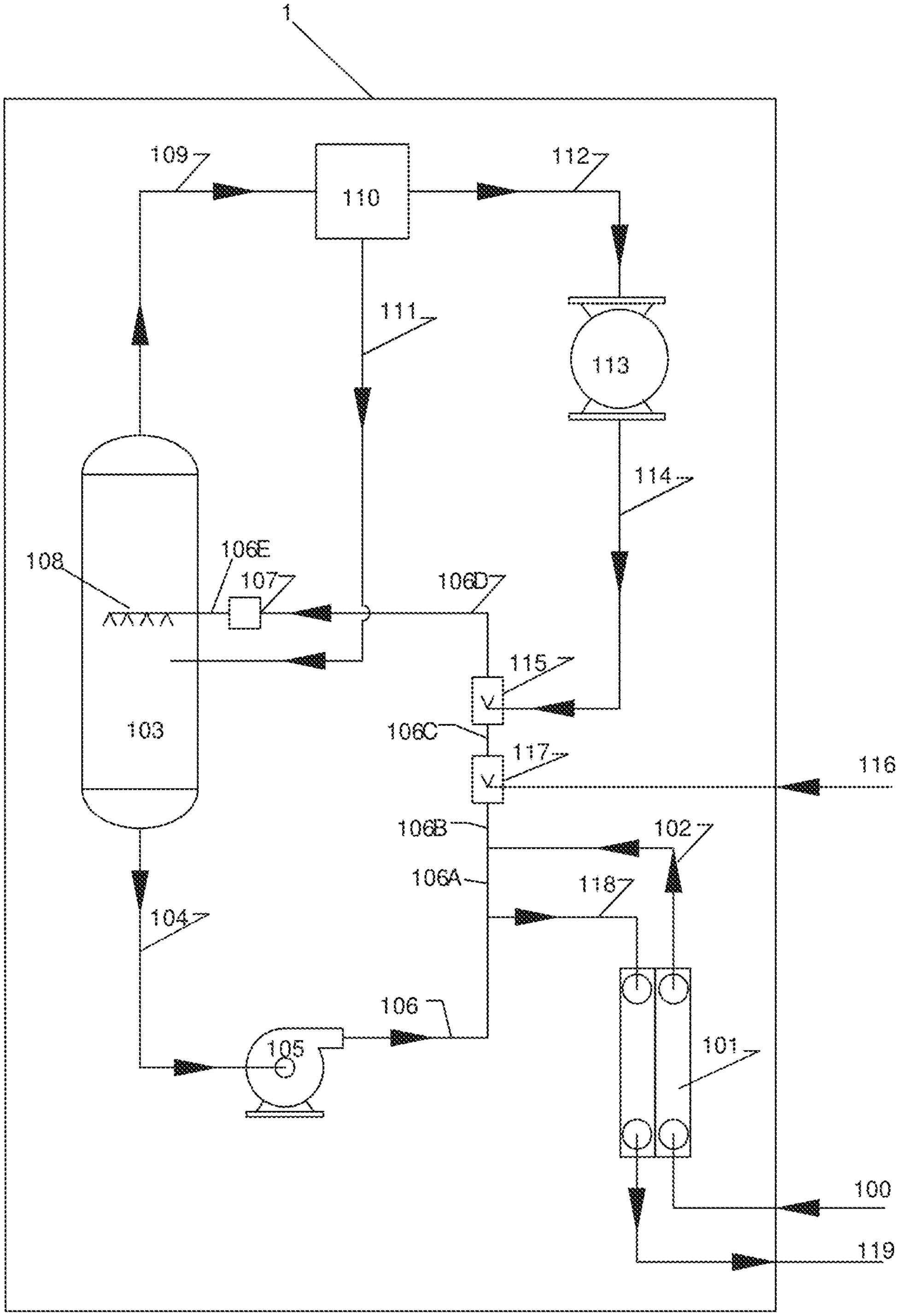
FIG. 1 is a schematic view of a system for treating biologically contaminated water in accordance with an exemplary embodiment.

Reference will now be made to the exemplary embodiments illustrated, and specific language will be used herein to describe the same. It will nevertheless be understood that no limitation of the scope of the invention is thereby intended.

DETAILED DESCRIPTION OF EXAMPLE EMBODIMENTS

Before invention embodiments are described, it is to be understood that this disclosure is not limited to the particular structures, process steps, or materials disclosed herein, but is extended to equivalents thereof as would be recognized by those ordinarily skilled in the relevant arts. It should also be understood that terminology employed herein is used for the purpose of describing particular examples or embodiments only and is not intended to be limiting. The same reference numerals in different drawings represent the same element. Numbers provided in flow charts and processes are provided for clarity in illustrating steps and operations and do not necessarily indicate a particular order or sequence.

Furthermore, the described features, structures, or characteristics can be combined in any suitable manner in one or more embodiments. In the following description, numerous specific details are provided, such as examples of compositions, dosage forms, treatments, etc., to provide a thorough understanding of various invention embodiments. One skilled in the relevant art will recognize, however, that such detailed embodiments do not limit the overall inventive concepts articulated herein, but are merely representative thereof.

It should be noted that as used herein, the singular forms "a," "an," and, "the" include plural referents unless the context clearly dictates otherwise. Thus, for example, reference to "a stream" includes reference to one or more of such streams, and reference to "the organism" includes reference to one or more of such organisms.

In this disclosure, "comprises," "comprising," "containing" and "having" and the like can have the meaning ascribed to them in U.S. Patent law and can mean "includes," "including," and the like, and are generally interpreted to be open ended terms. The terms "consisting of" or "consists of" are closed terms, and include only the components, structures, steps, or the like specifically listed in conjunction with such terms, as well as that which is in accordance with U.S. Patent law. "Consisting essentially of" or "consists essentially of" have the meaning generally ascribed to them by U.S. Patent law. In particular, such terms are generally closed terms, with the exception of allowing inclusion of additional items, materials, components, steps, or elements, that do not materially affect the basic and novel characteristics or function of the item(s) used in connection therewith. For example, trace elements present in a composition, but not affecting the compositions nature or characteristics would be permissible if present under the "consisting essentially of" language, even though not expressly recited in a list of items following such terminology. When using an open ended term, like "comprising" or "including," in the written description it is understood that direct support should be afforded also to "consisting essentially of" language as well as "consisting of" language as if stated explicitly and vice versa.

The terms "first," "second," "third," "fourth," and the like in the description and in the claims, if any, are used for distinguishing between similar elements and not necessarily for describing a particular sequential or chronological order. It is to be understood that any terms so used are interchangeable under appropriate circumstances such that the embodiments described herein are, for example, capable of operation in sequences other than those illustrated or otherwise described herein. Similarly, if a method is described herein as comprising a series of steps, the order of such steps as presented herein is not necessarily the only order in which such steps may be performed, and certain of the stated steps may possibly be omitted and/or certain other steps not described herein may possibly be added to the method.

As used herein, comparative terms such as "increased," "decreased," "better," "worse," "higher," "lower," "enhanced," "maximized," "minimized," and the like refer to a property of a device, component, composition, or activity that is measurably different from other devices, components, compositions or activities that are in a surrounding or adjacent area, that are similarly situated, that are in a single device or composition or in multiple comparable devices or compositions, that are in a group or class, that are in multiple groups or classes, or as compared to the known state of the art.

As used herein, the term "microorganism" refers to any organism that is too small to be individually viewed with a naked eye. Some microorganism may include a cell wall or other membrane, including a cellulosic or lipidic structure that houses internal organelles and components, such as nucleic acids, etc., and may further contain water or other fluids. Examples of such microorganisms can include without limitation, algae, bacteria, spores, virus, protozoa, etc. As used herein the term "pathogen" refers to any disease promoting microorganism.

As used herein, the term "biological wastewater," "biologically contaminated wastewater," and "biologically contaminated water" can be used interchangeably and these as well as like terms refer to a composition or solution (e.g. an aqueous solution) that contains a measureable amount of at least one microorganism.

The term "coupled," as used herein, is defined as directly or indirectly connected in a chemical, mechanical, electrical or nonelectrical manner. Objects described herein as being "adjacent to" each other may be in physical contact with each other, in close proximity to each other, or in the same general region or area as each other, as appropriate for the context in which the phrase is used. "Directly coupled" objects or elements are in physical contact with one another.

Occurrences of the phrase "in one embodiment," or "in one aspect," herein do not necessarily all refer to the same embodiment or aspect.

As used herein, the term "substantially" refers to the complete or nearly complete extent or degree of an action, characteristic, property, state, structure, item, or result. For example, an object that is "substantially" enclosed would mean that the object is either completely enclosed or nearly completely enclosed. The exact allowable degree of deviation from absolute completeness may in some cases depend on the specific context. However, generally speaking the nearness of completion will be so as to have the same overall result as if absolute and total completion were obtained. The use of "substantially" is equally applicable when used in a negative connotation to refer to the complete or near complete lack of an action, characteristic, property, state, structure, item, or result. For example, a composition that is "substantially free of" particles would either completely lack particles, or so nearly completely lack particles that the effect would be the same as if it completely lacked particles. In other words, a composition that is "substantially free of" an ingredient or element may still actually contain such item as long as there is no measurable effect thereof.

As used herein, the term "about" is used to provide flexibility to a numerical range endpoint by providing that a given value may be "a little above" or "a little below" the endpoint. Unless otherwise stated, use of the term "about" in accordance with a specific number or numerical range should also be understood to provide support for such numerical terms or range without the term "about". For example, for the sake of convenience and brevity, a numerical range of "about 50 angstroms to about 80 angstroms" should also be understood to provide support for the range of "50 angstroms to 80 angstroms." Furthermore, it is to be understood that in this specification support for actual numerical values is provided even when the term "about" is used therewith. For example, the recitation of "about" 30 should be construed as not only providing support for values a little above and a little below 30, but also for the actual numerical value of 30 as well.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

Concentrations, amounts, levels and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges or decimal units encompassed within that range as if each numerical value and sub-range is explicitly recited. As an illustration, a numerical range of "about 1 to about 5" should be interpreted to include not only the explicitly recited values of about 1 to about 5, but also include individual values and sub-ranges within the indicated range. Thus, included in this numerical range are individual values such as 2, 3, and 4 and sub-ranges such as from 1-3, from 2-4, and from 3-5, etc., as well as 1, 2, 3, 4, and 5, individually. This same principle applies to ranges reciting only one numerical value as a minimum or a maximum. Furthermore, such an interpretation should apply regardless of the breadth of the range or the characteristics being described.

Reference throughout this specification to "an example" means that a particular feature, structure, or characteristic described in connection with the example is included in at least one embodiment. Thus, appearances of the phrases "in an example" in various places throughout this specification are not necessarily all referring to the same embodiment.

The present disclosure sets forth a thermal system that uses heat to break down (lyse) organism (e.g. bacterial) cells in biologically contaminated water, such as waste activated sludge (WAS). For example, by increasing the temperature of a liquid above 100° C., bacterial cell walls will begin to weaken and rupture. Additionally, rapidly changing pressures will cause a bacterial cell to expand and/or contract based on the external pressures placed on the cell to further weaken and break down cell walls. The systems and methods disclosed herein can utilize one or both techniques to lyse the cells in the contaminated water, thereby releasing water that had been trapped inside the cell. Additionally, the increased temperature and rapid pressure changes serves to denature larger chain polymers and complex organic molecules in the contaminated water.

As will be described in more detail below, the present disclosure can utilize the addition of steam and pressure to heat the contaminated water in the system above a boiling temperature at standard atmospheric pressure. Then, using a pump, the system can cycle the boiling contaminated water across an orifice. This can continually raise and lower the liquid pressure thereby raising and lowering the pressure against organism cell walls in the contaminated water. Furthermore, the vapors created from active boiling in the system can be collected and compressed through a blower and then can be reinjected into the liquid stream. This can help recover the latent heat of evaporation from the boiling solution, increasing efficiency.

The system can accomplish cell lysis and denaturing of the contaminated water while being mindful to conserve energy. Outgoing contaminated water can be sent through a heat exchanger that can recover heat energy by transferring it back to the incoming contaminated water that is just entering. Additionally, as stated earlier, liberated water in the form of steam can be compressed and reinjected back into the incoming contaminated water to recover the latent heat of vaporization. In all, it is estimated that the system will be able to create complete cell destruction of the contaminated water stream at an energy demand of approximately 500 KWH/ton dry contaminated water solids. At a standard energy cost of $0.08/KWH, this is a cost of $40/ton dry contaminated water solids. In comparison, an estimated disposal cost of $50/wet ton contaminated water solids (which could be 5 times the volume of dry tons) is a common rate for landfill disposal in the country. Comparing these two values, utilizing the systems and methods set forth herein can result in a significant reduction of disposal costs. When considering that the pathogens will be also be killed in the contaminated water, the possibility of reuse increases instead of only considering the product for landfill disposal.

As mentioned above, the system can be used in conjunction with a digester. The system can improve the processing rate thereby allowing the digester to process larger flows within a smaller sized digester. In some examples, the system can implemented as a pretreatment in front of a digester and can manage the flow of a biologically contaminated wastewater stream to the digester. In some examples, the system can be configured as a slip stream circulating from the back of a digester to the front. In some examples, a digester can be an anaerobic digester.

Non-limiting examples of the systems and methods will now be described with reference to the figures. FIG. 1 is a schematic block diagram illustrating an embodiment of a system to provide water treatment services. The system 1 is provided that is operable to treat contaminated water by lysing cell walls to release water and fluid within the cells, thus making the water easier to filter and therefore minimizing the solids to dispose. The system 1 is further operable to destroy dangerous pathogens by temperature and residence time in accordance with EPA specifications, further contributing to making the solids easier to dispose.

The system 1 can include a biologically contaminated water feed stream 100 entering the system 1 and a treated water stream 119 leaving the system 1. The biologically contaminated water feed stream 100 can come from any upstream equipment or processes that produces contaminated water, such as but not limited to, waste activated sludge digesters (e.g. aerobic or anaerobic digesters), filters, centrifuges, hospitals, pharmaceutical manufacturing, food plants, etc. Furthermore, the contaminated water stream 100 can contain differing concentration ranges of solids (e.g. 0% to 30%). The treated water 119 leaving the system 1 can be sent for further treating or solids separation, which is not shown here. The solids content and volume of the treated water 119 can be the same or slightly more than the contaminated feed steam 100.

The system 1 takes the biologically contaminated water stream 100 and preheats it in a preheater exchanger 101 using the hot treated water stream 118 as a heat source. This recovers heat from the system 1 and makes the system 1 more efficient, thus helping to reduce energy costs associated with the system 1. The preheated biologically contaminated water stream 102 then joins a circulation stream 106.

The circulation of the contaminated water in the circulation stream 106 will now be described beginning with a flash vessel 103 shown in FIG. 1. The liquid in the bottom of the flash vessel 103 exits the flash vessel 103 to the circulation pump 105 suction via a line 104.

The circulation pump 105 is operable to raise the pressure of the contaminated water in the circulation stream 106. For example, the circulation pump 105 can increase the pressure of the circulation stream 106 from about 15 to about 100 PSIG. The flow rate through the circulation pump 105 can be, for example, from about 5 to about 400 times the flow rate of the biologically contaminated water feed 100. The circulation pump 105 discharges into the circulation stream 106. The main circulation 106 then splits into a part 106A of the main circulation stream 106 and into a hot treated water stream 118 that then enters the heat exchanger 101 and exits the system 1 as the treated water stream 119, as described above.

The circulation pump 105 can be a centrifugal, positive displacement, diaphragm, or other type of pump. The preheated contaminated water feed 102 joins with part 106A of the main circulation stream 106 to form part 106B of the main circulation stream 106. Compressed steam 114 from a blower 113 can be injected via a steam sparger 115 into the main circulation 106 at part 106B to heat the main circulation stream 106 at part 106C.

Makeup steam 116 can be introduced to the main circulation 106C via a steam sparger 117 to provide make up heat to the circulation stream 106 at part 106D. The makeup steam 116 can be provided from an external source to add heat energy to the system 1. The steam spargers 115 and 117 can be a perforated pipe, eductor, or other device that can mix the steam and liquid in the pipe. The heated part 106D of the main circulation stream 106 can then be flashed through a pressure drop device 107 to form steam in part 106E of the circulation stream 106 which can then be introduced to the flash sparger 108 in the flash vessel 103 where the steam and liquid are separated. The pressure drop device 107 can be an orifice plate, valve, gate, door, constriction (e.g. a venturi), filter, junction, bend, or other device or configuration that creates a pressure drop. The pressure drop device 107 is where much of the cell lysing can occur due to the high temperatures and change from high to low pressure. In some embodiments, the drop in pressure can be from about 100 PSIG to 50 PSIG. In some other embodiments, the drop can be from about 150 PSIG to about 15 PSIG. In some embodiments, the pressure drop can be from a higher pressure to a lower pressure can be from about a 10% drop in pressure to about a 90% drop in pressure. In other embodiments, the drop can be about 20%, 30%, 40%, 50%, 60%, 70%, 80%, or other percentage drops in between as needed in order to achieve a specific result. Such pressure drops can significantly contribute to the lysing of microcellular organisms as discussed herein. Temperatures in the main circulation stream 106 can range from 150 to 300 degrees Fahrenheit which is sufficient to destroy all pathogens that were introduced into the system 1 via the biologically contamination water stream 100.

To increase efficiency, steam from the flash vessel 103 can be captured and directed through line 109 to enter a mist eliminator 110 where any mist is separated from the steam. Liquid recovered from the mist eliminator 110 is directed through line 111 to be reintroduced to the flash vessel 103. The dry steam from the mist eliminator 110 can be directed through line 112 to be compressed in the blower 113. For example, the pressure on the outlet of the blower 113 can be between 5 and 30 PSIG. The blower 113 can be a rotary lobe, fan, centrifugal, or other type of compressor. The compressed steam from the blower 113 is directed through line 114 to be reintroduced to the main circulation stream 106 at part 106B via the steam sparger 115, as mentioned above. This process of steam capture and reintroduction helps to recover latent heat in the system 1 to increase its overall efficiency.

As mentioned above, hot treated water 118 from the main circulation 106 is separated from the circulation line 106 and is directed to the preheater 101 where it heats the biologically contaminated water feed 119 while cooling the treated water outlet stream 119. The preheater 101 can be a plate and frame, spiral, shell and tube, or other type of heat exchanger.

Figure 2:
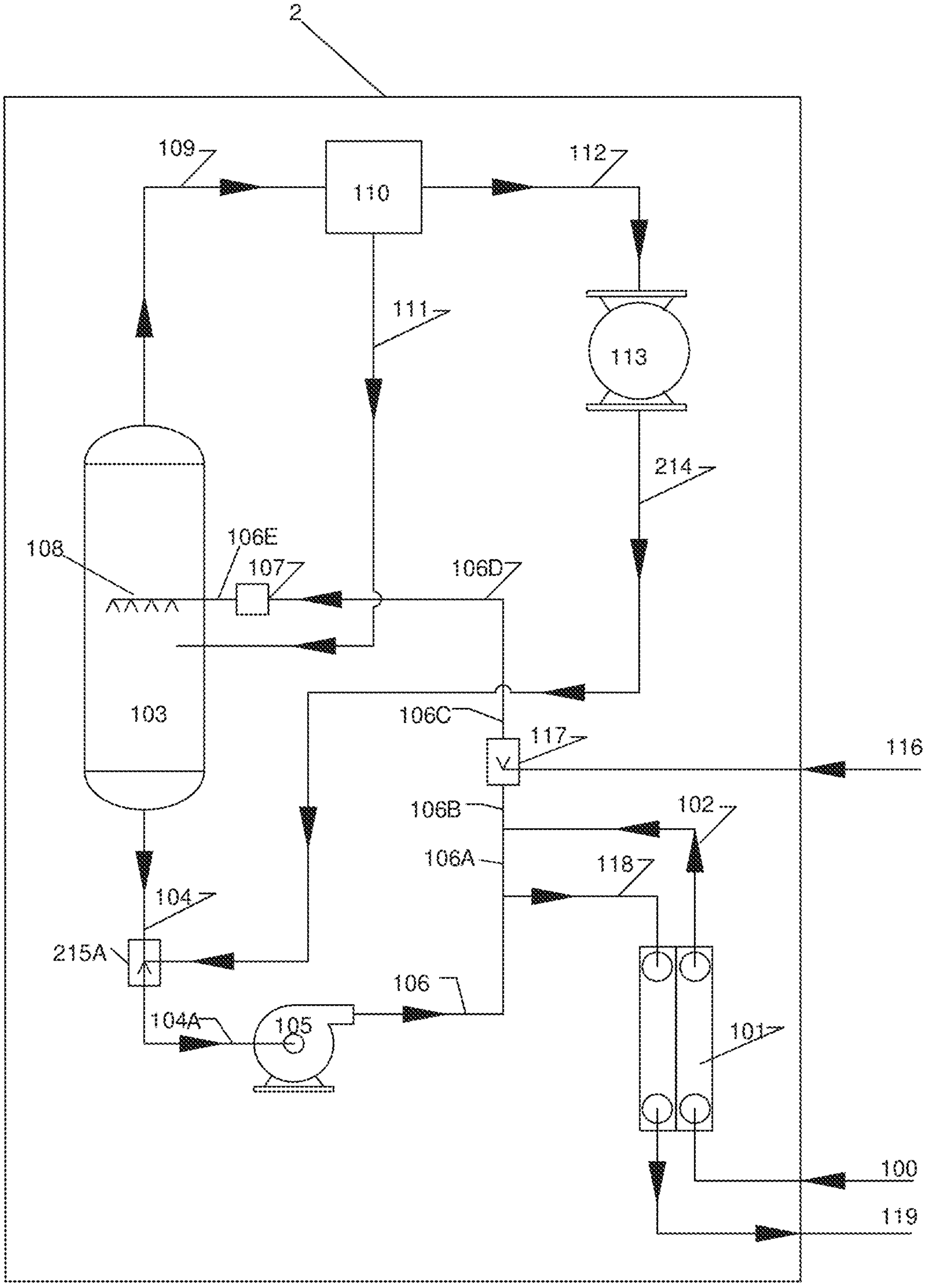
FIG. 2 is a schematic view of a system for treating biologically contaminated water in accordance with an exemplary embodiment.

FIG. 2 is a schematic block diagram illustrating another embodiment of a system to provide water treatment services. The system 2 shown in FIG. 2 is similar to FIG. 1 and like parts are labeled using like identifiers. The system 2 is operable to treat contaminated water by lysing cell walls, thus making the water easier to filter and therefore minimizing the solids to dispose. The system 2 is further operable to destroy dangerous pathogens by temperature and residence time in accordance with EPA specifications, further contributing to making the solids easier to dispose.

The system 2 can include a biologically contaminated water feed stream 100 entering the system 2 and a treated water stream 119 leaving the system 2. The biologically contaminated water feed stream 100 can come from any upstream equipment or processes that produces contaminated water such as but not limited to waste activated sludge digesters, filters, centrifuges, hospitals, pharmaceutical manufacturing, food plants, etc. Furthermore, the contaminated water stream 100 can contain from 0% to 30% solids. The treated water 119 leaving the system 2 can be sent for further treating or solids separation, which is not shown here. The solids content and volume of the treated water 119 can be the same or slightly more than the contaminated feed steam 100.

The system 2 takes the biologically contaminated water stream 100 and preheats it in a preheater exchanger 101 using the hot treated water stream 118 as a heat source. This recovers heat from the system 2 and makes the system 2 more efficient, thus helping to reduce energy costs associated with the system 2. The preheated biologically contaminated water stream 102 then joins a circulation stream 106.

The circulation of the contaminated water in the circulation stream 106 will now be described beginning with a flash vessel 103 shown in FIG. 2. The liquid in the bottom of the flash vessel 103 exits the flash vessel to the circulation pump 105 suction via line 104. Unlike system 1 shown in FIG. 1, compressed steam from the blower 113 is fed through line 214 to be injected via a steam sparger 215A into the line 104 of the main circulation stream 106 to further heat the main circulation stream 106 in part 104A. Part 104A of the main circulation stream then goes to the circulation pump 105.

The circulation pump 105 is operable to raise the pressure of the contaminated water in the circulation stream 106. For example, the circulation pump 105 can increase the pressure of the circulation stream 106 by 15 to 100 PSIG. The flow rate through the circulation pump 105 can be, for example, from 5 to 400 times the flow rate of the biologically contaminated water feed 100. The circulation pump 105 discharges into the circulation stream 106. The main circulation 106 then splits into a part 106A of the main circulation stream 106 and into a hot treated water stream 118 that then enters the heat exchanger 101 and exits the system 1 as the treated water stream 119, as described above.

The circulation pump 105 can be a centrifugal positive displacement, diaphragm, or other type of pump. The preheated contaminated water feed 102 joins with part 106A of the main circulation stream 106 to form part 106B of the main circulation stream 106. Makeup steam 116 can be introduced to the main circulation 106B via a steam sparger 117 to provide make up heat the circulation stream 106 at part 106C. The makeup steam 116 can be provided from an external source to add heat energy to the system 1.

The steam spargers 215A and 117 can be a perforated pipe, eductor or other device that can mix the steam and liquid in the pipe. The heated part 106D of the main circulation stream 106 can then be flashed through a pressure drop device 107 to form steam in part 106E of the circulation stream 106 which can then be introduced to the flash sparger 108 in the flash vessel 103 where the steam and liquid are separated. The pressure drop device 107 can be an orifice plate, valve, or other device that creates a pressure drop. The pressure drop device 107 is where much of the cell lysing can occur due to the high temperatures and change from high to low pressure. Temperatures in the main circulation stream 106 can range from 150 to 300 degrees Fahrenheit which is sufficient to destroy all pathogens that were introduced into the system 1 via the biologically contamination water stream 100.

To increase efficiency, steam from the flash vessel 103 can be captured and directed through line 109 to enter a mist eliminator 110 where any mist is separated from the steam. Liquid recovered from the mist eliminator 110 is directed through line 111 to be reintroduced to the flash vessel 103. The dry steam from the mist eliminator 110 can be directed through line 112 to be compressed in the blower 113. For example, the pressure on the outlet of the blower 113 can be between 5 and 30 PSIG. The blower 113 can be a rotary lobe, fan, centrifugal, or other type of compressor. The compressed steam from the blower 113 is then directed through line 214 to be reintroduced to the main circulation 106 via the steam sparger 215A, as mentioned above. This process of steam capture and reintroduction helps to recover latent heat in the system 2 to increase its overall efficiency.

As mentioned above, hot treated water 118 from the main circulation 106 is separated from the circulation line 106 and is directed to the preheater 101 where it heats the biologically contaminated water feed 119 while cooling the treated water outlet stream 119. The preheater 101 can be a plate and frame, spiral, shell and tube, or other type of heat exchanger.

Figure 3:
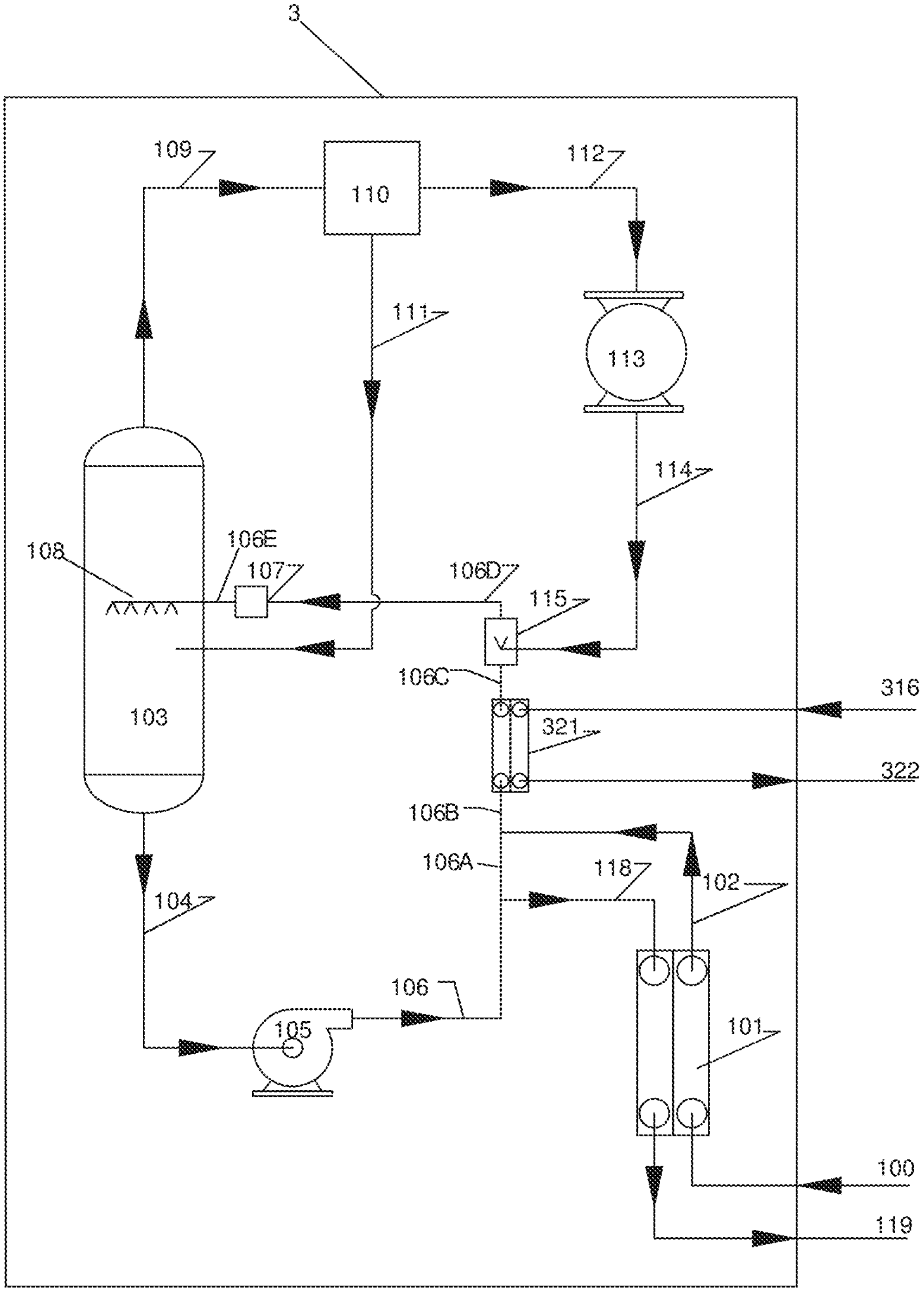
FIG. 3 is a schematic view of a system for treating biologically contaminated water in accordance with an exemplary embodiment.

FIG. 3 is a schematic block diagram illustrating another embodiment of a system to provide water treatment services. The system 3 shown in FIG. 3 is similar to FIGS. 1 and 2, and like parts are labeled using like identifiers. The system 3 is operable to treat contaminated water by lysing cell walls, thus making the water easier to filter and therefore minimizing the solids to dispose. The system 3 is further operable to destroy dangerous pathogens by temperature and residence time in accordance with EPA specifications, further contributing to making the solids easier to dispose.

The system 3 can include a biologically contaminated water feed stream 100 entering the system 3 and a treated water stream 119 leaving the system 3. The biologically contaminated water feed stream 100 can come from any upstream equipment or processes that produces contaminated water such as but not limited to waste activated sludge digesters, filters, centrifuges, hospitals, pharmaceutical manufacturing, food plants, etc. Furthermore, the contaminated water stream 100 can contain from 0% to 30% solids. The treated water 119 leaving the system 3 can be sent for further treating or solids separation, which is not shown here. The solids content and volume of the treated water 119 can be the same or slightly more than the contaminated feed steam 100.

The system 3 takes the biologically contaminated water stream 100 and preheats it in a preheater exchanger 101 using the hot treated water stream 118 as a heat source. This recovers heat from the system 3 and makes the system 3 more efficient, thus helping to reduce energy costs associated with the system 3. The preheated biologically contaminated water stream 102 then joins a circulation stream 106.

The circulation of the contaminated water in the circulation stream 106 will now be described beginning with a flash vessel 103 shown in FIG. 3. The liquid in the bottom of the flash vessel 103 exits the flash vessel 103 to the circulation pump 105 suction via a line 104.

The circulation pump 105 is operable to raise the pressure of the contaminated water in the circulation stream 106. For example, the circulation pump 105 can increase the pressure of the circulation stream 106 by 15 to 100 PSIG. The flow rate through the circulation pump 105 can be, for example, from 5 to 400 times the flow rate of the biologically contaminated water feed 100. The circulation pump 105 discharges into the circulation stream 106. The main circulation 106 then splits into a part 106A of the main circulation stream 106 and into a hot treated water stream 118 that then enters the heat exchanger 101 and exits the system 1 as the treated water stream 119, as described above.

The circulation pump 105 can be a centrifugal, positive displacement, diaphragm, or other type of pump. The preheated contaminated water feed 102 joins with part 106A of the main circulation stream 106 to form part 106B of the main circulation stream 106.

As shown in FIG. 3, part 106B of the circulation stream 106 can be directed into a heat exchanger 321. The heat exchanger comprises a heat input 316 that is taken from an external source to provide heat to the heat exchanger 321. A return line 322 is provided exiting the heat exchanger 321. In some embodiments, the heat input 316 and the return line 322 can be part of a closed loop fluid flow to bring heat to the system 3 from an external source. The heat exchanger 321 adds heat energy to the main circulation stream 106 which exits the heat exchanger 321 at part 106C of the main circulation stream.

Compressed steam 114 from a blower 113 can be injected via a steam sparger 115 into the main circulation 106 at part 106C to further heat the main circulation stream 106 at part 106D. The steam sparger 115 can be a perforated pipe, eductor, or other device that can mix the steam and liquid in the pipe. The heated part 106D of the main circulation stream 106 can then be flashed through a pressure drop device 107 to form steam in part 106E of the circulation stream 106 which can then be introduced to the flash sparger 108 in the flash vessel 103 where the steam and liquid are separated. The pressure drop device 107 can be an orifice plate, valve, or other device that creates a pressure drop. The pressure drop device 107 is where much of the cell lysing can occur due to the high temperatures and change from high to low pressure. Temperatures in the main circulation stream 106 can range from 150 to 300 degrees Fahrenheit which is sufficient to destroy all pathogens that were introduced into the system 1 via the biologically contamination water stream 100.

In some embodiments, the pressure increase on the circulation stream can induce or cause lysing of cellular microorganisms (e.g. bacteria). In other embodiments, the drop or change in pressure on the circulation stream can be induce or otherwise cause lysing of cellular microorganisms. In yet another embodiment, the heat exerted on the circulation stream can induce or otherwise cause lysing of cellular microorganisms. In further embodiments, a combination of two or more of the above (e.g. pressure increase, pressure drop, or temperature) can induce or otherwise cause lysing of cellular microorganisms in the circulation stream. In some embodiments, one or more of these conditions (e.g. any individually, any combination of two, or a combination of all three) can be sufficient to between 5% and 100% of cellular microorganisms in the circulation stream. In another embodiment, one or more of these conditions or events can be sufficient to lyse from 20% to 100% of cellular microorganism in the circulation stream. In another embodiment, the amount of cellular microorganisms lysed can be greater than 50%, 60%, 70%, 80%, 90%, or 95%. In some embodiments, one or more of these conditions or events can kill, destroy, or otherwise deactivate or inactivate other non-cellular pathogens in the circulation stream, such as viruses and other nucleic acid materials (e.g. by denaturation, etc.). As previously mentioned, the lysing of cellular materials, including cellular microorganisms and release of liquid (e.g. water) and other internal materials can dramatically reduced the resultant solids output by the system and allow further recapture or diversion of water.

To increase efficiency, steam from the flash vessel 103 can be captured and directed through line 109 to enter a mist eliminator 110 where any mist is separated from the steam. Liquid recovered from the mist eliminator 110 is directed through line 111 to be reintroduced to the flash vessel 103. The dry steam from the mist eliminator 110 can be directed through line 112 to be compressed in the blower 113. For example, the pressure on the outlet of the blower 113 can be between 5 and 30 PSIG. The blower 113 can be a rotary lobe, fan, centrifugal, or other type of compressor. The compressed steam from the blower 113 is directed through line 114 to be reintroduced to the main circulation stream 106 at part 106C via the steam sparger 115, as mentioned above. This process of steam capture and reintroduction helps to recover latent heat in the system 1 to increase its overall efficiency.

As mentioned above, hot treated water 118 from the main circulation 106 is separated from the circulation line 106 and is directed to the preheater 101 where it heats the biologically contaminated water feed 119 while cooling the treated water outlet stream 119. The preheater 101 can be a plate and frame, spiral, shell and tube, or other type of heat exchanger.

While the forgoing examples are illustrative of the principles of the present invention in one or more particular applications, it will be apparent to those of ordinary skill in the art that numerous modifications in form, usage and details of implementation can be made without the exercise of inventive faculty, and without departing from the principles and concepts of the invention. Accordingly, it is not intended that the invention be limited, except as by the claims set forth below.

What is claimed is:

1. A method of harvesting water from a microorganism in a biologically contaminated water stream comprising:

preheating a biologically contaminated water stream using heat from a treated water stream;

adding the preheated biologically contaminated water stream to a circulation stream;

pressurizing and adding heat to the circulation stream;

dropping the pressure of the circulation stream;

separating steam from liquid in the circulation stream;

compressing the steam and reintroducing all of the steam into the circulation stream; and outputting the treated water stream from the circulation stream.

2. The method of claim 1, wherein the circulation stream is pressurized between the separating of the steam from the liquid and the adding of the preheated biologically contaminated water stream to the circulation stream.

3. The method of claim 1, further comprising adding additional heat to the circulation stream after adding the preheated biologically contaminated water stream to the circulation stream.

4. The method of claim 1, further comprising extracting a liquid stream from the steam prior to compressing the steam and adding the liquid stream to the circulation stream.

5. The method of claim 1, wherein the steam is reintroduced to the circulation stream prior to pressuring the circulation stream.

* * * * *